United States Patent
Kubanek et al.

(10) Patent No.: US 8,487,135 B2
(45) Date of Patent: *Jul. 16, 2013

(54) CATALYST AND PROCESS FOR PREPARING AN AMINE

(75) Inventors: Petr Kubanek, Mannheim (DE); Wolfgang Mägerlein, Mannheim (DE); Johann-Peter Melder, Böhl-Iggelheim (DE); Thomas Heidemann, Viernheim (DE)

(73) Assignee: BASF SE, Ludwigshafen (DE)

( * ) Notice: Subject to any disclaimer, the term of this patent is extended or adjusted under 35 U.S.C. 154(b) by 236 days.

This patent is subject to a terminal disclaimer.

(21) Appl. No.: 12/958,545

(22) Filed: Dec. 2, 2010

(65) Prior Publication Data

US 2011/0137030 A1    Jun. 9, 2011

(30) Foreign Application Priority Data

Dec. 3, 2009   (EP) .................................. 09177914

(51) Int. Cl.
| | | |
|---|---|---|
| C07C 209/16 | (2006.01) | |
| C07D 265/30 | (2006.01) | |
| C07D 295/03 | (2006.01) | |
| C07D 241/04 | (2006.01) | |
| B01J 31/00 | (2006.01) | |
| B01J 23/10 | (2006.01) | |

(52) U.S. Cl.
USPC ........... 564/480; 564/479; 544/106; 544/178; 544/358; 502/113

(58) Field of Classification Search
USPC ....................................................... 564/480
See application file for complete search history.

(56) References Cited

U.S. PATENT DOCUMENTS

| | | | |
|---|---|---|---|
| 3,275,554 | A | 9/1966 | Wagenaar |
| 3,751,475 | A | 8/1973 | van der Voort et al. |
| 4,832,702 | A | 5/1989 | Kummer et al. |
| 5,530,127 | A | 6/1996 | Reif et al. |
| 5,916,838 | A | 6/1999 | Wulff-Doring et al. |
| 5,958,825 | A | 9/1999 | Wulff-Doring et al. |
| 6,147,261 | A | 11/2000 | Knifton et al. |
| 6,525,222 | B2 | 2/2003 | Nouwen et al. |
| 6,534,441 | B1 | 3/2003 | Bartley et al. |
| 6,821,396 | B2 | 11/2004 | Wolfert et al. |
| 6,986,833 | B2 | 1/2006 | Wolfert et al. |
| 7,034,186 | B2 | 4/2006 | Gerlach et al. |
| 7,183,438 | B2 | 2/2007 | Gerlach et al. |
| 2008/0255351 | A1 | 10/2008 | Hoffer et al. |
| 2009/0286977 | A1 | 11/2009 | Kubanek et al. |
| 2010/0274010 | A1 | 10/2010 | Kubanek et al. |
| 2010/0274055 | A1 | 10/2010 | Kubanek et al. |
| 2011/0137029 | A1 | 6/2011 | Kubanek et al. |

FOREIGN PATENT DOCUMENTS

| | | |
|---|---|---|
| DE | 2125039 A1 | 12/1971 |
| DE | 1953263 A1 | 2/1972 |
| DE | 2844984 A1 | 4/1979 |
| DE | 3611230 A1 | 10/1987 |
| EP | 0514692 A2 | 11/1992 |
| EP | 0696572 A1 | 2/1996 |
| EP | 839574 A2 | 5/1998 |
| EP | 0839575 A2 | 5/1998 |
| EP | 0963975 A1 | 12/1999 |
| EP | 0967011 | 12/1999 |
| EP | 1106600 A2 | 6/2001 |
| EP | 1312599 A1 | 5/2003 |
| EP | 1312600 A1 | 5/2003 |
| EP | 1431271 A1 | 6/2004 |
| GB | 1319495 A | 6/1973 |
| GB | 2006773 A | 5/1979 |
| WO | WO-98/26868 A1 | 6/1998 |
| WO | WO-03/051508 A1 | 6/2003 |
| WO | WO-03/076386 A2 | 9/2003 |
| WO | WO-2004/084887 A1 | 10/2004 |
| WO | WO-2007/036496 A1 | 4/2007 |
| WO | WO-2008/006750 A1 | 1/2008 |
| WO | WO2009/080506 | 7/2009 |
| WO | WO-2009/080506 A1 | 7/2009 |
| WO | WO-2009/080507 A1 | 7/2009 |
| WO | WO2009/080508 | 7/2009 |
| WO | WO-2009/080508 A1 | 7/2009 |
| WO | WO2009/080509 | 7/2009 |
| WO | WO2009/080510 | 7/2009 |
| WO | WO2009/080514 | 7/2009 |
| WO | WO2009/080515 | 7/2009 |
| WO | WO-2009/114438 A2 | 9/2009 |
| WO | WO2010/031719 | 3/2010 |
| WO | WO2011/067199 | 6/2011 |
| WO | WO2011/067200 | 6/2011 |

OTHER PUBLICATIONS

International Search Report, PCT/EP2010/068375, mailed May 24, 2011.
Eng. Translation of International Preliminary Report on Patent ability, PCT/EP2010/068375, Nov. 29, 2010.
Written Opinion, PCT/EP2010/068375, Nov. 29, 2010.
Eng. Translation of International Preliminary Report on Patent ability, PCT/EP2010/068376, Nov. 29, 2010.
Written Opinion, PCT/EP2010/068376, Nov. 29, 2010.
ISO 9277: 1995, (2003).
A. B. Stiles, Catalyst Manufacture—Laboratory and Commercial Preparations, Marcel Dekker, New York, (1983) p. 14-19
Ullmann's Encyclopedia of Industrial Chemistry, 5th Ed., vol. B 4, pp. 199-238 "Fixed-Bed Reactors", (1992).

*Primary Examiner* — Brian J Davis
(74) *Attorney, Agent, or Firm* — Novak Druce Connolly Bove + Quigg LLP

(57) ABSTRACT

A process for preparing an amine by reacting a primary or secondary alcohol, aldehyde and/or ketone with hydrogen and a nitrogen compound selected from the group of ammonia and primary and secondary amines, in the presence of a supported copper-, nickel- and cobalt-containing catalyst, wherein the catalytically active material of the catalyst, before the reduction thereof with hydrogen, comprises oxygen compounds of aluminum, of copper, of nickel and of cobalt, and in the range from 0.2 to 5.0% by weight of oxygen compounds of tin, calculated as SnO, and catalysts as defined above.

41 Claims, No Drawings

US 8,487,135 B2

CATALYST AND PROCESS FOR PREPARING AN AMINE

CROSS-REFERENCE TO RELATED APPLICATIONS

This application claims benefit of European application 09177914.0, filed Dec. 3, 2009, the contents of which are incorporated herein by reference in its entirety.

FIELD OF THE INVENTION

The present invention relates to aluminum oxide-, copper-, nickel- and cobalt-containing catalysts, and to a process for preparing an amine by reacting a primary or secondary alcohol, aldehyde and/or ketone with hydrogen and a nitrogen compound selected from the group of ammonia and primary and secondary amines, in the presence of a supported copper-, nickel- and cobalt-containing catalyst.

BACKGROUND

The process products find use, inter alia, as intermediates in the preparation of fuel additives (U.S. Pat. Nos. 3,275,554 A; DE 21 25 039 A and DE 36 11 230 A), surfactants, medicaments and crop protection compositions, hardeners for epoxy resins, catalysts for polyurethanes, intermediates for preparation of quaternary ammonium compounds, plasticizers, corrosion inhibitors, synthetic resins, ion exchangers, textile assistants, dyes, vulcanization accelerants and/or emulsifiers.

EP 963 975 A1 and EP 1 106 600 A2 (both BASF AG) describe processes for preparing amines from, respectively, alcohols and aldehydes or ketones, and nitrogen compounds, using a catalyst whose catalytically active material comprises 22-40% by weight (and 22-45% by weight) of oxygen compounds of zirconium, 1-30% by weight of oxygen compounds of copper and 15-50% by weight (and 5-50% by weight) each of oxygen compounds of nickel and of cobalt.

WO 03/076386 A and EP 1 431 271 A1 (both BASF AG) also teach catalysts of the abovementioned type for aminations. No Sn content is taught.

EP 514 692 A2 (BASF AG) relates to a process for preparing amines from alkanols in the presence of catalysts comprising Cu, Ni, optionally Co, $ZrO_2$ and/or $Al_2O_3$.

The preferred catalyst consists of 55% by weight of $Al_2O_3$, 36% by weight of Cu and 7% by weight of Ni (example 1). No Sn content is taught.

WO 03/051508 A1 (Huntsman Petrochemical Corp.) relates to processes for aminating alcohols using specific Cu/Ni/Zr/Sn-containing catalysts which, in a further configuration, comprise Cr instead of Zr (see page 4 lines 10-16). The catalysts described in this WO application do not comprise any aluminum oxide or any cobalt.

WO 2007/036496 A (BASF AG) describes a process for preparing aminodiglycol (ADG) and morpholine by reacting diethylene glycol (DEG) with ammonia in the presence of a transition metal heterogeneous catalyst, wherein the catalytically active material of the catalyst, before the treatment with hydrogen, comprises oxygen compounds of aluminum and/or zirconium, of copper, of nickel and of cobalt, and the shaped catalyst body has specific dimensions. No Sn content is taught.

DE 28 44 984 A1 (Shell Int. Res.) describes processes for preparing an amine by reacting an alcohol, aldehyde or ketone having up to 25 carbon atoms with ammonia or a primary or secondary amine over a catalyst which comprises Cu, Sn and optionally alkali metal or alkaline earth metal on a porous support, for example aluminum oxide. These catalysts do not comprise any nickel or any cobalt.

EP 839 574 A2 and EP 839 575 A2 (both BASF AG) describe catalysts for aminating alcohols, which comprise Ni, Co, Cu, Ru on a porous metal oxide support, for example aluminum oxide, silicon dioxide, titanium dioxide, zirconium dioxide, inter alia. Sn is mentioned among numerous possible promoters. The catalyst activity and catalyst stability are in need of improvement.

U.S. Pat. No. 6,147,261 (Shell Oil Corp.) teaches nickel and/or cobalt catalysts for amination of particular hydroxyalkanals, which optionally comprise a support, for example aluminum oxide, magnesium oxide, silica, inter alia. Preferred catalysts are Raney cobalt and Raney nickel. The catalysts described do not comprise Sn.

U.S. Pat. No. 6,534,441 B1 (Union Carbide) describes catalysts for the reductive amination of lower aliphatic alkane derivatives, the active material of which is said to profit from a synergistic effect of Ni and Re. Such catalysts are based on an aluminosilicate support with 5-65% by weight of silica. The catalysts may also comprise a promoter from numerous groups of the Periodic Table, including group IVA (Sn), IB (Cu), VIII (Ni, Co).

WO 98/26868 A1 (Batelle Memorial Institute) describes catalysts for reactions in the aqueous phase based on Ni, which comprise a promoter from the group of Cu, Sn, Ag, Re, Ru, or a combination thereof. The promoter content is <5% by weight. The amination of alcohols/aldehydes/ketones is not described. Nor is an aluminum oxide support one of the supports described.

WO 2004/084887 A1 (DuPont) claims a process for preparing pyrrolidone derivatives from levulinic acid and aromatic amines (reductive amination). Numerous different catalysts comprising noble metals in particular on different supports, also including alumina, are used. Sn is not present.

DE 19 53 263 A (BASF AG) discloses catalysts comprising cobalt, nickel and copper on aluminum oxide with a metal content of 5 to 80% by weight, especially 10 to 30% by weight, based on the overall catalyst, where the catalysts comprise, calculated on the metal content, 70 to 95% by weight of a mixture of cobalt and nickel, and 5 to 30% by weight of copper. For example, the catalyst possesses the composition of 10% by weight of CoO, 10% by weight of NiO and 4% by weight of CuO on $Al_2O_3$. The catalyst does not comprise Sn, and the catalyst activity and catalyst stability are in need of improvement.

WO 2008/006750 A1 (BASF AG) relates to particular Pb-, Bi-, Sn-, Sb- and/or In-doped, zirconium dioxide-, copper-, nickel- and cobalt-containing catalysts, and to the use thereof in processes for preparing an amine by reacting a primary or secondary alcohol, aldehyde and/or ketone with hydrogen and ammonia or a primary or secondary amine. Aluminum oxide supports are not taught.

WO 2009/080507 A1 (BASF SE) relates to particular Sn- and Co-doped, zirconium dioxide-copper- and nickel-containing catalysts, and to the use thereof in processes for preparing an amine by reacting a primary or secondary alcohol, aldehyde and/or ketone with hydrogen and ammonia or a primary or secondary amine. Aluminum oxide supports are not taught.

WO 2009/080506 A1 (BASF SE) describes particular Pb-, Bi-, Sn-, Mo-, Sb- and/or P-doped, zirconium dioxide-, nickel- and iron-containing catalysts, and the use thereof in processes for preparing an amine by reacting a primary or secondary alcohol, aldehyde and/or ketone with hydrogen and ammonia or a primary or secondary amine. Aluminum oxide supports are not taught. The catalysts preferably do not comprise Cu or Co.

WO 2009/080508 A1 (BASF SE) teaches particular Pb-, Bi-, Sn- and/or Sb-doped, zirconium dioxide-, copper-, nickel-, cobalt- and iron-containing catalysts, and the use thereof in processes for preparing an amine by reacting a primary or secondary alcohol, aldehyde and/or ketone with hydrogen and ammonia or a primary or secondary amine. Aluminum oxide supports are not taught.

WO 2009/114438 A2 (Huntsman Petrochem. Corp.) relates to the amination of cyclohexanedimethanol in the presence of hydrogen and $ZrO_2$-supported metal catalysts, e.g. $ZrO_2/Cu/Ni/Sn$.

In the course of amination of diethylene glycol (DEG), there is, for example, an increased extent of formation of undesired methoxyethanol or methoxyethylamine. Methoxyethanol is toxic, can be removed from morpholine only with difficulty owing to its physical properties, and can thus lead to problems with regard to specification and product quality.

In the example of the amination of diethylene glycol (DEG), "decarbonylation" is considered more particularly to be the sum of undesired components (methanol, methoxyethanol, methoxyethylamine, N-methylmorpholine and methoxyethylmorpholine), which form from DEG via methoxyethanol according to the reaction scheme:

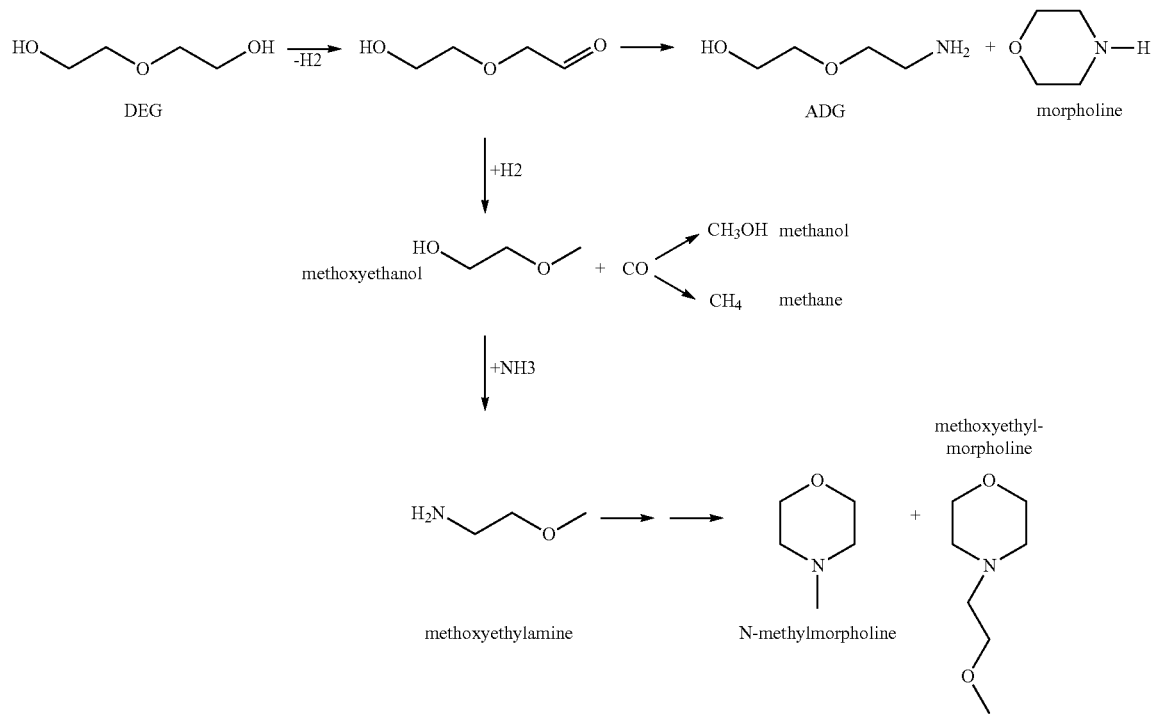

A parallel European patent application with the same filing date (BASF SE) relates to particular doped aluminum oxide-, copper-, nickel-, cobalt- and tin-containing catalysts, and to the use thereof in processes for preparing an amine from a primary or secondary alcohol, aldehyde and/or ketone.

In the case of use of the very active prior art catalysts, including in particular the catalysts according to EP 963 975 A1 and EP 1 106 600 A2 (see above), there may be an increased extent of decarbonylation of the carbonyl function (which may have formed as an intermediate) in the reactants (alcohols, aldehydes, ketones) at elevated temperature. As a result of the large amount of heat of hydrogenation released, the formation of methane by hydrogenation of carbon monoxide (CO) leads to a 'runaway risk', i.e. an uncontrolled temperature rise in the reactor. When CO is scavenged by amines, secondary components containing methyl groups are formed.

Furthermore, in the case of use of the very active prior art amination catalysts, in particular of those based on zirconium dioxide, there may be undesired ether cleavage, which necessitates improvement in the yield of products of economic interest, for example ADG and morpholine (MOR).

The reaction mechanism of the amination of primary or secondary alcohols is assumed to be that the alcohol is first dehydrogenated over a metal site to the corresponding aldehyde. In this context, the copper or else nickel is probably of particular significance as a dehydrogenating component. When aldehydes are used for the amination, this step is absent.

The aldehyde formed or used can be aminated by reaction with ammonia or primary or secondary amine with elimination of water and subsequent hydrogenation. This condensation of the aldehyde with the abovementioned nitrogen compound is probably catalyzed by acidic sites of the catalyst. However, the aldehyde can also be decarbonylated in an undesired side reaction, which means that the aldehyde function is eliminated as CO. The decarbonylation or methanization probably takes place over a metal site. The CO is hydrogenated to methane over the hydrogenation catalyst, and so the methane formation indicates the extent of decarbonylation. The decarbonylation forms the abovementioned undesired by-products, for example methoxyethanol and/or methoxyethylamine in the abovementioned case.

The desired condensation of the aldehyde with ammonia or primary or secondary amine and the undesired decarbonylation of the aldehyde are parallel reactions, of which the desired condensation is probably acid-catalyzed, whereas the undesired decarbonylation is catalyzed by metallic sites.

BRIEF SUMMARY

It was an object of the present invention to improve the economic viability of existing processes for hydrogenating amination of aldehydes or ketones and the amination of alcohols, and to remedy one or more disadvantages of the prior art, especially the abovementioned disadvantages. The intention was to find catalysts which are preparable industrially in a simple manner and which allow the above-mentioned aminations to be performed with high conversion, high yield, space-time yields (STY), selectivity, with simultaneously high mechanical stability of the shaped catalyst body and low 'runaway risk'. The catalysts should accordingly have a high activity and, under the reaction conditions, a high chemical and mechanical stability. Furthermore, the use of the catalysts in corresponding amination processes, in which linear and cyclic process products can result owing to the chemical structure of the reactants, should lead with improved selectivity to the linear process product(s). More particularly, the intention was also to find catalysts which lead to higher yields of products of economic interest, for example aminodiglycol and morpholine, proceeding from DEG.

[Space-time yields are reported in 'Amount of product/(Catalyst volume·time)' (kg/($I_{cat}$·h)) and/or 'Amount of product/(Reactor volume·time)' (kg/($I_{reactor}$·h)].

Accordingly, a process has been found for preparing an amine by reacting a primary or secondary alcohol, aldehyde and/or ketone with hydrogen and a nitrogen compound selected from the group of ammonia and primary and secondary amines, in the presence of a supported copper-, nickel- and cobalt-containing catalyst, wherein the catalytically active material of the catalyst, before the reduction thereof with hydrogen, comprises oxygen compounds of aluminum, of copper, of nickel and of cobalt, and in the range from 0.2 to 5.0% by weight of oxygen compounds of tin, calculated as SnO.

In addition, catalysts have been found, whose catalytically active material, before the reduction thereof with hydrogen, comprises oxygen compounds of aluminum, of copper, of nickel and of cobalt, and in the range from 0.2 to 5.0% by weight of oxygen compounds of tin, calculated as SnO.

More particularly, catalysts have been found, whose catalytically active material, before the reduction thereof with hydrogen, comprises in the range from
15 to 80% by weight of oxygen compounds of aluminum, calculated as $Al_2O_3$,
1 to 20% by weight of oxygen compounds of copper, calculated as CuO,
5 to 35% by weight of oxygen compounds of nickel, calculated as NiO,
5 to 35% by weight of oxygen compounds of cobalt, calculated as CoO, and
0.2 to 5.0% by weight of oxygen compounds of tin, calculated as SnO,
and the use thereof in the abovementioned amination process, especially in the process for reacting DEG with ammonia.

All figures regarding the composition of the catalytically active material of the inventive catalysts and those used in the process according to the invention are based on the catalytically active material before the reduction thereof with hydrogen.

DETAILED DESCRIPTION OF THE PREFERRED EMBODIMENTS

There is no indication in the literature that the specific combination of nickel, copper, cobalt, tin and aluminum oxide leads more particularly to a synergistic effect and that these catalysts are advantageous compared to the prior art in the amination of alcohols/aldehydes/ketones, more particularly better with regard to overall selectivity and process reliability.

It has been recognized in accordance with the invention that the activity of the catalyst for amination of primary or secondary alcohols, aldehydes and/or ketones in the presence of $H_2$, for example the amination of diethylene glycol (DEG) with ammonia to give aminodiglycol and morpholine, as a result of the content of cobalt and the additional specific content of Sn in the aluminum oxide-copper-nickel catalysts, essentially at least remains the same, but, at the same time, the extent of the undesired decarbonylation reaction decreases and hence the selectivity of the amination reaction increases. At the same time, the extent of undesired high boiler formation is suppressed and hence the selectivity of the amination reaction is improved.

The process can be performed continuously or batchwise. Preference is given to a continuous method.

For the synthesis in the gas phase, the reactants are fed to the reactor in a controlled manner, preferably in a cycle gas stream, evaporated and in gaseous form. Suitable amines for a gas phase synthesis are amines which, owing to their boiling points and the boiling points of their reactants, can be kept in the gas phase within the process parameters by process technology means. The cycle gas serves firstly to evaporate the reactants and secondly as a reactant for the amination.

In the cycle gas method, the starting materials (alcohol, aldehyde and/or ketone, hydrogen and the nitrogen compound) are evaporated in a cycle gas stream and fed to the reactor in gaseous form.

The reactants (alcohol, aldehyde and/or ketone, the nitrogen compound) may also be evaporated as aqueous solutions and passed to the catalyst bed with the cycle gas stream.

Preferred reactors are tubular reactors. Examples of suitable reactors with cycle gas stream can be found in Ullmann's Encyclopedia of Industrial Chemistry, 5th Ed., Vol. B 4, pages 199-238, "Fixed-Bed Reactors".

Alternatively, the reaction is advantageously effected in a tube bundle reactor or in a single-stream plant.

In a single-stream plant, the tubular reactor in which the reaction proceeds can consist of a series connection of a plurality of (e.g. two or three) individual tubular reactors. Optionally, an intermediate introduction of feed (comprising the reactant and/or ammonia and/or $H_2$) and/or cycle gas and/or reactor effluent from a downstream reactor is possible here in an advantageous manner.

The cycle gas flow rate is preferably in the range from 40 to 1500 $m^3$ (at operating pressure)/[$m^3$ of catalyst (bed volume) ·h], in particular in the range from 100 to 700 $m^3$ (at operating pressure)/[$m^3$ of catalyst (bed volume)·h].

The cycle gas comprises preferably at least 10% by volume, particularly from 50 to 100% by volume, very particularly from 80 to 100% by volume of $H_2$.

For the synthesis in the liquid phase, suitable reactants and products are all of those which have high boiling points or are thermally labile. In these cases, a further advantage is that it is possible to dispense with evaporation and recondensation of the amine in the process.

In the process according to the invention, the catalysts are preferably used in the form of catalysts which consist only of catalytically active material and, if appropriate, a shaping assistant (for example graphite or stearic acid) if the catalyst is used as a shaped body, i.e. do not comprise any further catalytically active ingredients. In this connection, the oxidic support material aluminum oxide ($Al_2O_3$) is considered to be included in the catalytically active material.

The catalysts are used in such a way that the catalytically active material ground to powder is introduced into the reaction vessel or that the catalytically active material, after grinding, mixing with shaping assistants, shaping and heat treatment, is arranged in the reactor as shaped catalyst bodies—for example as tablets, spheres, rings, extrudates (e.g. strands).

The concentration figures (in % by weight) of the components of the catalyst are based in each case, unless stated otherwise, on the catalytically active material of the finished catalyst after its last heat treatment and before its reduction with hydrogen.

The catalytically active material of the catalyst, after its last heat treatment and before its reduction with hydrogen, is defined as the sum of the masses of the catalytically active constituents and of the abovementioned catalyst support materials, and comprises essentially the following constituents:
aluminum oxide ($Al_2O_3$), oxygen compounds of copper, of nickel and of cobalt, and oxygen compounds of tin.

The sum of the abovementioned constituents of the catalytically active material is typically from 70 to 100% by weight, preferably from 80 to 100% by weight, more preferably from 90 to 100% by weight, particularly >95% by weight, very particularly >98% by weight, in particular >99% by weight, for example more preferably 100% by weight.

The catalytically active material of the inventive catalysts and of those used in the process according to the invention may also comprise one or more elements (oxidation stage 0) or their inorganic or organic compounds selected from groups I A to VI A and I B to VII B and VIII of the Periodic Table of the Elements.

Examples of such elements and compounds thereof are: transition metals such as Mn or $MnO_2$, W or tungsten oxides, Ta or tantalum oxides, Nb or niobium oxides or niobium oxalate, V or vanadium oxides or vanadyl pyrophosphate; lanthanides such as Ce or $CeO_2$ or Pr or $Pr_2O_3$; alkaline earth metal oxides such as SrO; alkaline earth metal carbonates such as $MgCO_3$, $CaCO_3$ and $BaCO_3$; boron oxide ($B_2O_3$).

The catalytically active material of the inventive catalysts and of those used in the process according to the invention preferably does not comprise any rhenium, any ruthenium, any iron and/or any zinc, in each case either in metallic (oxidation state=0) form or in an ionic (oxidation state≠0), especially oxidized, form.

The catalytically active material of the inventive catalysts and of those used in the process according to the invention preferably does not comprise any silver and/or molybdenum, in each case either in metallic (oxidation state=0) form or in an ionic (oxidation state≠0), especially oxidized, form.

In a particularly preferred embodiment, the catalytically active material of the inventive catalysts and of those used in the process according to the invention does not comprise any further catalytically active component, either in elemental (oxidation state=0) form or in an ionic (oxidation state≠0) form.

In the particularly preferred embodiment, the catalytically active material is not doped with further metals or metal compounds.

Preferably, however, typical accompanying trace elements originating from the metal extraction of Cu, Co, Ni, Sn are excluded therefrom.

The catalytically active material of the catalyst preferably does not comprise any oxygen compounds of silicon, of zirconium and/or of chromium.

The catalytically active material of the catalyst, before the reduction thereof with hydrogen, comprises in the range from 0.2 to 5.0% by weight, particularly in the range from 0.4 to 4.0% by weight, more particularly in the range from 0.6 to 3.0% by weight, even more preferably in the range from 0.7 to 2.5% by weight, of oxygen compounds of tin, calculated as SnO.

The catalytically active material of the catalyst, before the reduction thereof with hydrogen, comprises in the range from 5.0 to 35% by weight, particularly in the range from 10 to 30% by weight, more particularly in the range from 12 to 28% by weight, very particularly 15 to 25% by weight, of oxygen compounds of cobalt, calculated as CoO.

The catalytically active material of the catalyst, before the reduction thereof with hydrogen, comprises additionally preferably in the range from
15 to 80% by weight, particularly 30 to 70% by weight, more particularly 35 to 65% by weight, of oxygen compounds of aluminum, calculated as $Al_2O_3$,
1 to 20% by weight, particularly 2 to 18% by weight, more particularly 5 to 15% by weight, of oxygen compounds of copper, calculated as CuO, and
5 to 35% by weight, particularly 10 to 30% by weight, more particularly 12 to 28% by weight, very particularly 15 to 25% by weight, of oxygen compounds of nickel, calculated as NiO.

The molar ratio of nickel to copper is preferably greater than 1, more preferably greater than 1.2, even more preferably in the range from 1.8 to 8.5.

The BET surface area (ISO 9277:1995) of the inventive catalysts and of those used in the process according to the invention is preferably in the range from 30 to 250 $m^2/g$, particularly in the range from 90 to 200 $m^2/g$, more particularly in the range from 130 to 190 $m^2/g$. Theses ranges are achieved more particularly by calcining temperatures in the course of catalyst preparation in the range from 400 to 600° C., particularly 420 to 550° C., (see below).

To prepare the catalysts used in the process according to the invention, various processes are possible. They are, for example, obtainable by peptizing pulverulent mixtures of the hydroxides, carbonates, oxides and/or other salts of the components with water and subsequently extruding and heat-treating the material thus obtained.

Preference is given to preparing the inventive catalysts by employing precipitation methods. For example, they can be obtained by coprecipitating the nickel, cobalt, copper and Sn components from an aqueous salt solution comprising these elements by means of bases in the presence of a slurry of a sparingly soluble, oxygen-containing aluminum compound and subsequently washing, drying and calcining the resulting precipitate. The sparingly soluble oxygen-containing aluminum compounds used may, for example, be aluminum oxide, aluminum oxide hydrate, aluminum phosphates, aluminum borates and aluminum silicates. The slurries of the sparingly soluble aluminum compounds can be prepared by suspending fine powders of these compounds in water with vigorous stirring. Advantageously, these slurries are obtained by precipitating the sparingly soluble aluminum compounds from aqueous aluminum salt solutions by means of bases.

The inventive catalysts are preferably prepared by means of a coprecipitation (mixed precipitation) of all of their components. To this end, an aqueous salt solution comprising the catalyst components is appropriately admixed with an aqueous base—for example sodium carbonate, sodium hydroxide, potassium carbonate or potassium hydroxide—under hot conditions with stirring until the precipitation is complete. It is also possible to work with alkali metal-free bases such as ammonia, ammonium carbonate, ammonium hydrogencarbonate, ammonium carbamate, ammonium oxalate, ammonium malonate, urotropin, urea, etc. The type of salts used is generally not critical: since the principal factor in this procedure is the water solubility of the salts, a criterion is their good water solubility required to prepare these comparatively highly concentrated salt solutions. It is considered to be self-evident that, when selecting the salts of the individual components, the salts selected will of course only be those with anions which do not lead to disruption, whether by causing undesired precipitations or by complicating or preventing the precipitation by complex formation.

The precipitates obtained in these precipitation reactions are generally chemically inhomogeneous and consist, inter alia, of mixtures of the oxides, oxide hydrates, hydroxides, carbonates and insoluble and basic salts of the metals used. It may be found to be favorable for the filterability of the precipitates when they are aged, i.e. when they are left for a certain time after the precipitation, if appropriate under hot conditions or while passing air through.

The precipitates obtained by these precipitation processes are processed further as usual to give the inventive catalysts. First, the precipitates are washed. The content of alkali metal which has been supplied by the (mineral) base which may have been used as a precipitant can be influenced via the duration of the washing operation and via the temperature and amount of the washing water. In general, prolonging the washing time or increasing the temperature of the washing water will decrease the content of alkali metal. After the washing, the precipitated material is generally dried at 80 to 200° C., preferably at 100 to 150° C., and then calcined. The calcination is performed generally at temperatures between 300 and 800° C., preferably at 400 to 600° C., in particular at 420 to 550° C.

The inventive catalysts may also be prepared by impregnating aluminum oxide ($Al_2O_3$) which is present, for example, in the form of powder or shaped bodies such as extrudates, tablets, spheres or rings.

The aluminum oxide is used, for example, in the amorphous, gamma, theta and/or delta form, as aluminum oxohydroxide (boehmite), preferably in the amorphous form.

Shaped bodies can be produced by the customary processes.

The impregnation is likewise effected by the customary processes, as described, for example, in A. B. Stiles, Catalyst Manufacture—Laboratory and Commercial Preparations, Marcel Dekker, New York (1983), by applying an appropriate metal salt solution in each case in one or more impregnation stages, the metal salts used being, for example, appropriate nitrates, acetates or chlorides. After the impregnation, the material is dried and optionally calcined.

The impregnation can be effected by the so-called incipient wetness method, in which the aluminum oxide is moistened, in accordance with its water uptake capacity, up to a maximum of saturation with the impregnation solution. The impregnation can also be effected in supernatant solution.

In the case of multistage impregnation processes, it is appropriate to dry and optionally to calcine between individual impregnation steps. Multistage impregnation can be employed advantageously particularly when the aluminum oxide is to be loaded with a relatively large amount of metal.

To apply the metal components to the aluminum oxide, the impregnation can be effected simultaneously with all metal salts or successively in any sequence of the individual metal salts.

Subsequently, the catalysts prepared by impregnation are dried and preferably also calcined, for example within the calcination temperature ranges already specified above.

After the calcination, the catalyst is appropriately conditioned, whether it be by grinding to a certain particle size or by mixing it, after it has been ground, with shaping assistants such as graphite or stearic acid, compressing it by means of a press to moldings, for example tablets, and heat-treating. The heat treatment temperatures correspond preferably to the temperatures in the calcining.

The catalysts prepared in this way comprise the catalytically active metals in the form of a mixture of their oxygen compounds, i.e. in particular in the form of oxides and mixed oxides.

The catalysts prepared, for example, as described above are stored as such and, if appropriate, treated. Before they are used as catalysts, they are typically prereduced. However, they can also be used without prereduction, in which case they are reduced under the conditions of the hydrogenating amination by the hydrogen present in the reactor.

For prereduction, the catalysts are exposed to a nitrogen-hydrogen atmosphere first at preferably 150 to 200° C. over a period of, for example, 12 to 20 hours, and then treated in a hydrogen atmosphere at preferably 200 to 400° C. for another up to approx. 24 hours. This prereduction reduces a portion of the oxygen-containing metal compounds present in the catalysts to the corresponding metals, so that they are present together with the different types of oxygen compounds in the active form of the catalyst.

A further advantage of the inventive catalysts is their mechanical stability, i.e. their hardness. The mechanical stability can be determined by the measurement of the so-called side crushing strength. For this purpose, the shaped catalyst body, for example the catalyst tablet, is stressed with increasing force between two parallel plates until fracture of the shaped catalyst body occurs, and this stress may act, for example, on the cylindrical surface of catalyst tablets. The force registered when the shaped catalyst body fractures is the side crushing strength.

The process according to the invention is preferably performed continuously, the catalyst preferably being arranged in the reactor as a fixed bed. It is possible for the flow toward the fixed catalyst bed to be either from the top or from the bottom. The gas stream is adjusted in terms of temperature, pressure and flow rate in such a way that even relatively high-boiling reaction products remain in the gas phase.

The aminating agent may, with regard to the alcoholic hydroxyl group or aldehyde group or keto group to be aminated, be used in stoichiometric, sub- or superstoichiometric amounts.

In the case of the amination of alcohols, aldehydes or ketones with primary or secondary amines, the amine is preferably used in an approximately stoichiometric amount or slightly superstoichiometric amount per mole of alcoholic hydroxyl group, aldehyde group or keto group to be aminated.

The amine component (nitrogen compound) is used preferably in 0.90 to 100 times the molar amount, especially in 1.0 to 10 times the molar amount, based in each case on the alcohol, aldehyde and/or ketone used.

Especially ammonia is used generally with a 1.5- to 250-fold, preferably 2- to 100-fold, especially 2- to 10-fold molar excess per mole of alcoholic hydroxyl group, aldehyde group or keto group to be converted.

Higher excesses both of ammonia and of primary or secondary amines are possible.

Preference is given to employing an offgas flow rate of 5 to 800 standard cubic meters/h, especially 20 to 300 standard cubic meters/h (standard cubic meters=volume converted to standard conditions).

The amination of the primary or secondary alcohol groups, aldehyde groups or keto groups of the reactant can be performed in the liquid phase or in the gas phase. Preference is given to the fixed bed process in the gas phase.

When working in the liquid phase, the reactants (alcohol, aldehyde or ketone plus ammonia or amine) are passed simultaneously, including hydrogen, over the catalyst, which is typically disposed in a fixed bed reactor preferably heated externally, in the liquid phase at pressures of generally 5 to 30 MPa (50-300 bar), preferably 5 to 25 MPa, more preferably 15 to 25 MPa, and temperatures of generally 80 to 350° C., particularly 100 to 300° C., preferably 120 to 270° C., more preferably 130 to 250° C., in particular 170 to 230° C. Both a trickle mode and a liquid-phase mode are possible. The catalyst hourly space velocity is generally in the range from 0.05 to 5 kg, preferably 0.1 to 2 kg and more preferably 0.2 to 0.6 kg of alcohol, aldehyde or ketone per liter of catalyst (bed volume) and hour. If appropriate, the reactants can be diluted with a suitable solvent such as tetrahydrofuran, dioxane, N-methylpyrrolidone or ethylene glycol dimethyl ether. It is appropriate to heat the reactants before they are fed into the reaction vessel, preferably to the reaction temperature.

When working in the gas phase, the gaseous reactants (alcohol, aldehyde or ketone plus ammonia or amine) are passed over the catalyst in the presence of hydrogen in a gas stream, preferably hydrogen, selected so as to be sufficiently large for evaporation, at pressures of generally 0.1 to 40 MPa (1 to 400 bar), preferably 0.1 to 10 MPa, more preferably 0.1 to 5 MPa. The temperatures for the amination of alcohols are generally 80 to 350° C., particularly 100 to 300° C., preferably 120 to 270° C., more preferably 160 to 250° C. The reaction temperatures in the hydrogenating amination of aldehydes and ketones are generally 80 to 350° C., particularly 90 to 300° C., preferably 100 to 250° C. The flow to the fixed catalyst bed may be either from above or from below. The required gas stream is preferably obtained by a cycle gas method.

The catalyst hourly space velocity is generally in the range from 0.01 to 2 and preferably 0.05 to 0.5 kg of alcohol, aldehyde or ketone per liter of catalyst (bed volume) and hour.

The hydrogen is fed to the reaction generally in an amount of 5 to 400 l, preferably in an amount of 50 to 200 l per mole of alcohol, aldehyde or ketone component, the amounts in liters each having been converted to standard conditions (S.T.P.).

The performance of the amination of aldehydes or ketones differs from that of the amination of alcohols in that at least stoichiometric amounts of hydrogen need to be present in the amination of aldehydes and ketones.

Both in the case of operation in the liquid phase and in the case of operation in the gas phase, it is possible to use higher temperatures and higher overall pressures and catalyst hourly space velocities. The pressure in the reaction vessel, which results from the sum of the partial pressures of the aminating agent, of the alcohol, aldehyde or ketone, and of the reaction products formed and, if appropriate, of the solvent used at the temperatures specified, is appropriately increased by injecting hydrogen up to the desired reaction pressure.

Both in the case of continuous operation in the liquid phase and in the case of continuous operation in the gas phase, the excess aminating agent can be circulated together with the hydrogen.

When the catalyst is arranged as a fixed bed, it may be advantageous for the selectivity of the reaction to mix the shaped catalyst bodies in the reactor with inert packings, to "dilute" them as it were. The proportion of packings in such catalyst preparations may be 20 to 80 parts by volume, particularly 30 to 60 parts by volume and in particular 40 to 50 parts by volume.

The water of reaction formed in the course of the reaction (in each case one mole per mole of alcohol group, aldehyde group or keto group converted) generally does not have a disruptive effect on the degree of conversion, the reaction rate, the selectivity and the catalyst lifetime, and is therefore appropriately not removed therefrom until the workup of the reaction product, for example by distillation.

After the reaction effluent has appropriately been decompressed, the excess hydrogen and any excess aminating agent present are removed therefrom and the resulting crude reaction product is purified, for example by a fractional rectification. Suitable workup processes are described, for example, in EP 1 312 600 A and EP 1 312 599 A (both BASF AG). The excess aminating agent and the hydrogen are advantageously returned back into the reaction zone. The same applies to any incompletely converted alcohol, aldehyde or ketone component.

Unconverted reactants and any suitable by-products which are obtained can be returned back into the synthesis. Unconverted reactants can be flowed again in the cycle gas stream over the catalyst bed in batchwise or continuous mode after condensation of the products in the separator.

Aminating agents in the process according to the invention are, as well as ammonia, primary and secondary amines.

It is possible by the process according to the invention to prepare, for example, amines of the formula I

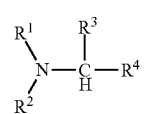

in which

R$^1$, R$^2$ are each hydrogen (H), alkyl such as C$_{1-20}$-alkyl, cycloalkyl such as C$_{3-12}$-cycloalkyl, alkoxyalkyl such as C$_{2-30}$-alkoxyalkyl, dialkylaminoalkyl such as C$_{3-30}$-dialkylaminoalkyl, aryl, aralkyl such as C$_{7-20}$-aralkyl and alkylaryl such as C$_{7-20}$-alkylaryl, or together are —(CH$_2$)$_j$—X—(CH$_2$)$_k$—, R$^3$, R$^4$ are each hydrogen (H), alkyl such as C$_{1-20}$-alkyl, cycloalkyl such as C$_{3-12}$-cycloalkyl, hydroxyalkyl such as C$_{1-20}$-hydroxyalkyl, aminoalkyl such as C$_{1-20}$-aminoalkyl, hydroxyalkylaminoalkyl such as C$_{2-20}$-hydroxyalkylaminoalkyl, alkoxyalkyl such as C$_{2-30}$-alkoxyalkyl, dialkylaminoalkyl such as C$_{3-30}$-dialkylamino-alkyl, alkylaminoalkyl such as C$_{2-30}$-alkylaminoalkyl, R$^5$—(OCR$^6$R$^7$CR$^8$R$^9$)$_n$—(OCR$^6$R$^7$), aryl, heteroaryl, aralkyl such as C$_{4-20}$-aralkyl, heteroarylalkyl such as C$_{4-20}$-heteroarylalkyl, alkylaryl such as C$_{7-20}$-alkylaryl, alkylheteroaryl such as C$_{4-20}$-alkylheteroaryl, and Y—(CH$_2$)$_m$—NR$^5$—(CH$_2$)$_q$ or, together, —(CH$_2$)$_j$—X—(CH$_2$)$_m$— or $R^2$ and $R^4$ together are —$(CH_2)_j$—X—$(CH_2)_m$—, $R^5$, $R^{10}$ are each hydrogen (H), alkyl such as $C_{1-4}$-alkyl, alkylphenyl such as $C_{7-40}$-alkylphenyl, $R^6$, $R^7$, $R^8$, $R^9$ are each hydrogen (H), methyl or ethyl, X is $CH_2$, $CHR^5$, oxygen (O), sulfur (S) or $NR^5$, Y is $N(R^{10})_2$, hydroxyl, $C_{2-20}$-alkylaminoalkyl or $C_{3-20}$-dialkylaminoalkyl, n is an integer of 1 to 30 and j, k, l, m, q are each integers of 1 to 4.

The process according to the invention therefore preferably finds use for preparing an amine I by reacting a primary or secondary alcohol of the formula II

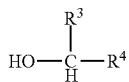
(II)

and/or an aldehyde and/or a ketone of the formula VI or VII

(VI)

(VII)

with a nitrogen compound of the formula III

(III)

where $R^1$, $R^2$, $R^3$ and $R^4$ are each as defined above.

The reactant alcohol may also be an amino alcohol, for example an amino alcohol of the formula II.

As is evident from the definitions of the $R^2$ and $R^4$ radicals, the reaction can also be effected intramolecularly in an appropriate amino alcohol, amino ketone or amino aldehyde.

To prepare the amine I, in a purely formal sense, a hydrogen atom of the nitrogen compound III is accordingly replaced by the $R^4(R^3)CH$— radical with release of one molar equivalent of water.

The process according to the invention preferably also finds use in the preparation of a cyclic amine of the formula IV

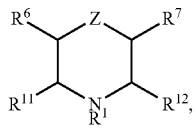
(IV)

in which $R^{11}$ and $R^{12}$ are each hydrogen (H), alkyl such as $C_1$- to $C_{20}$-alkyl, cycloalkyl such as $C_3$- to $C_{12}$-cycloalkyl, aryl, heteroaryl, aralkyl such as $C_7$- to $C_{20}$-aralkyl, and alkylaryl such as $C_7$- to $C_{20}$-alkylaryl, Z is $CH_2$, $CHR^5$, oxygen (O), $NR^5$ or $NCH_2CH_2OH$ and $R^1$, $R^6$, $R^7$ are each as defined above, by reacting an alcohol of the formula V

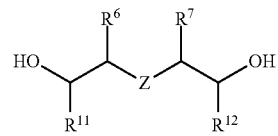
(V)

with ammonia or a primary amine of the formula VIII

$R^1$—$NH_2$ (VIII).

The substituents $R^1$ to $R^{12}$, the variables X, Y, Z, and the indices j, k, l, m, n and q in the compounds I, II, III, IV, V, VI and VII are each independently defined as follows:

$R^1$, $R^2$, $R^3$, $R^4$, $R^5$, $R^6$, $R^7$, $R^8$, $R^9$, $R^{10}$, $R^{11}$, $R^{12}$: hydrogen (H), $R^3$, $R^4$:
  alkyl such as $C_{1-20}$-alkyl, preferably $C_{1-14}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, hydroxyalkyl such as $C_{1-20}$-hydroxyalkyl, preferably $C_{1-8}$-hydroxyalkyl, more preferably $C_{1-4}$-hydroxyalkyl, such as hydroxymethyl, 1-hydroxyethyl, 2-hydroxy-ethyl, 1-hydroxy-n-propyl, 2-hydroxy-n-propyl, 3-hydroxy-n-propyl and 1-(hydroxy-methyl)ethyl, aminoalkyl such as $C_{1-20}$-aminoalkyl, preferably $C_{1-8}$-aminoalkyl, such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl) aminomethyl, hydroxyalkylaminoalkyl such as $C_{2-20}$-hydroxyalkylaminoalkyl, preferably $C_{3-8}$-hydroxyalkylaminoalkyl, such as (2-hydroxyethylamino)methyl, 2-(2-hydroxyethylamino)ethyl and 3-(2-hydroxyethylamino)propyl, $R^5$—$(OCR^6R^7CR^8R^9)_n$—$(OCR^6R^7)$, preferably $R^5$—$(OCHR^7CHR^9)_n$—$(OCR^6R^7)$, more preferably $R^5$—$(OCH_2CHR^9)_n$—$(OCR^6R^7)$, alkylaminoalkyl such as $C_{2-30}$-alkylaminoalkyl, preferably $C_{2-20}$-alkylaminoalkyl, more preferably $C_{2-8}$-alkylaminoalkyl, such as methylaminomethyl, 2-methyl-aminoethyl, ethylaminomethyl, 2-ethylaminoethyl and 2-(isopropylamino)ethyl, $(R^5)HN$—$(CH_2)_q$, Y—$(CH_2)_m$—$NR^5$—$(CH_2)_q$, heteroarylalkyl such as $C_{4-20}$-heteroarylalkyl, such as pyrid-2-ylmethyl, furan-2-ylmethyl, pyrrol-3-ylmethyl and imidazol-2-ylmethyl, alkylheteroaryl such as $C_{4-20}$-alkylheteroaryl, such as 2-methyl-3-pyridinyl, 4,5-di-methylimidazol-2-yl, 3-methyl-2-furanyl and 5-methyl-2-pyrazinyl, heteroaryl such as $C_{3-5}$-heteroaryl having at least one heteroatom from N, O, such as 2-pyridinyl, 3-pyridinyl, 4-pyridinyl, pyrazinyl, pyrrol-3-yl, imidazol-2-yl, 2-furanyl and 3-furanyl, $R^1$, $R^2$, $R^3$, $R^4$:
  cycloalkyl such as $C_{3-12}$-cycloalkyl, preferably $C_{3-8}$-cycloalkyl, such as cyclopropyl, cyclobutyl, cyclopentyl, cyclohexyl, cycloheptyl and cyclooctyl, more preferably cyclopentyl and cyclohexyl, alkoxyalkyl such as $C_{2-30}$-alkoxyalkyl, preferably $C_{2-20}$-alkoxyalkyl, more preferably $C_{2-8}$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, more preferably $C_{2-4}$-alkoxyalkyl, dialkylaminoalkyl such as $C_{3-30}$-dialkylaminoalkyl, preferably $C_{3-20}$-dialkylamino-alkyl, more preferably $C_{3-10}$-dialkylaminoalkyl, such as N,N-dimethylaminomethyl, (N,N-dibutylamino)methyl, 2-(N,N-dimethylamino)ethyl, 2-(N,N-diethyl-amino)ethyl, 2-(N,N-dibutylamino)ethyl, 2-(N,N-di-n-propylamino)ethyl and 2-(N,N-diisopropylamino)ethyl, 3-(N,N-dimethylamino)propyl, $(R^5)_2N$—$(CH_2)_q$, aryl such as $C_{6-14}$-aryl, such as phenyl, 1-naphthyl, 2-naphthyl, 1-anthryl, 2-anthryl and 9-anthryl, preferably phenyl, 1-naphthyl and 2-naphthyl, more preferably phenyl, alkylaryl such as $C_{7-20}$-alkylaryl, preferably $C_{7-12}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, aralkyl such as $C_{7-20}$-aralkyl, preferably $C_{7-12}$-phenylalkyl, such as benzyl, p-methoxybenzyl, 3,4-dimethoxybenzyl, 1-phenethyl, 2-phenethyl, 1-phenyl-propyl, 2-phenylpropyl, 3-phenylpropyl, 1-phenylbutyl, 2-phenylbutyl, 3-phenyl-butyl and 4-phenylbutyl, more preferably benzyl, 1-phenethyl and 2-phenethyl, $R^3$ and $R^4$ or $R^2$ and $R^4$ together are a —$(CH_2)_j$—X—$(CH_2)_m$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^1, R^2$:
alkyl such as $C_{1-20}$-alkyl, preferably $C_{1-8}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, more preferably $C_{1-4}$-alkyl, or $R^1$ and $R^2$ together are a —$(CH_2)_j$—X—$(CH_2)_k$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^5, R^{10}$:
alkyl, preferably $C_{1-4}$-alkyl, such as methyl, ethyl, n-propyl, isopropyl, n-butyl, isobutyl, sec-butyl and tert-butyl, preferably methyl and ethyl, more preferably methyl, alkylphenyl, preferably $C_{7-40}$-alkylphenyl, such as 2-methylphenyl, 3-methyl-phenyl, 4-methylphenyl, 2,4-dimethylphenyl, 2,5-dimethylphenyl, 2,6-dimethyl-phenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, in particular $C_{7-20}$-alkylphenyl, $R^6, R^7, R^8, R^9$:
methyl or ethyl, preferably methyl, $R^{11}, R^{12}$:
alkyl such as $C_1$- to $C_{20}$-alkyl, cycloalkyl such as $C_3$- to $C_{12}$-cycloalkyl, aryl, heteroaryl, aralkyl such as $C_7$- to $C_{20}$-aralkyl, and alkylaryl such as $C_7$- to $C_{20}$-alkylaryl, in each case as defined above, X:
$CH_2$, $CHR^5$, oxygen (O), sulfur (S) or $NR^5$, preferably $CH_2$ and O, Y:
$N(R^{10})_2$, preferably $NH_2$ and $N(CH_3)_2$,
hydroxyl (OH),
$C_{2-20}$-alkylaminoalkyl, preferably $C_{2-16}$-alkylaminoalkyl, such as methylamino-methyl, 2-methylaminoethyl, ethylaminomethyl, 2-ethylaminoethyl and 2-(iso-propylamino)ethyl,
$C_{3-20}$-dialkylaminoalkyl, preferably $C_{3-16}$-dialkylaminoalkyl, such as dimethylamino-methyl, 2-dimethylaminoethyl, 2-diethylaminoethyl, 2-(di-n-propylamino)ethyl and 2-(diisopropylamino)ethyl, Z:
$CH_2$, $CHR^5$, O, $NR^5$ or $NCH_2CH_2OH$, j, l:
an integer of 1 to 4 (1, 2, 3 or 4), preferably 2 and 3, more preferably 2, k, m, q:
an integer of 1 to 4 (1, 2, 3 or 4), preferably 2, 3 and 4, more preferably 2 and 3, n:
an integer of 1 to 30, preferably an integer of 1 to 8 (1, 2, 3, 4, 5, 6, 7 or 8), more preferably an integer of 1 to 6.

Suitable alcohols under the abovementioned prerequisites are virtually all primary and secondary alcohols with an aliphatic OH function. The alcohols may be straight-chain, branched or cyclic. Secondary alcohols are aminated just as efficiently as primary alcohols. The alcohols may also bear substituents or comprise functional groups which behave inertly under the conditions of the hydrogenating amination, for example alkoxy, alkenyloxy, alkylamino or dialkylamino groups, or else if appropriate are hydrogenated under the conditions of the hydrogenating amination, for example CC double or triple bonds. When polyhydric alcohols, for example, diols or triols, particularly glycols, are to be aminated, it is possible via the control of the reaction conditions to obtain preferentially amino alcohols, cyclic amines or polyaminated products.

The amination of 1,2-diols leads, depending on the selection of the reaction conditions, particularly to 1-amino-2-hydroxy compounds or 1,2-diamino compounds.

The amination of 1,4-diols leads, depending on the selection of the reaction conditions, to 1-amino-4-hydroxy compounds, 1,4-diamino compounds, or to five-membered rings with a nitrogen atom (pyrrolidines).

The amination of 1,6-diols leads, depending on the selection of the reaction conditions, to 1-amino-6-hydroxy compounds, 1,6-diamino compounds, or to seven-membered rings with a nitrogen atom (hexamethyleneimines).

The amination of 1,5-diols leads, depending on the selection of the reaction conditions, to 1-amino-5-hydroxy compounds, 1,5-diamino compounds, or to six-membered rings with a nitrogen atom (piperidines, 1,5-dipiperidinylpentanes).

It is accordingly possible to obtain from diglycol (DEG), by amination with $NH_3$, monoaminodiglycol (=ADG=H$_2$N—CH$_2$CH$_2$—O—CH$_2$CH$_2$—OH), diaminodiglycol (H$_2$N—CH$_2$CH$_2$—O—CH$_2$CH$_2$—NH$_2$) or morpholine. Particular preference is given here to ADG as the process product.

Piperazine is correspondingly obtained with particular preference from diethanolamine. N-(2-Hydroxyethyl)piperazine can be obtained from triethanolamine.

Preference is given to aminating, for example, the following alcohols:

methanol, ethanol, n-propanol, isopropanol, n-butanol, isobutanol, n-pentanol, n-hexanol, 2-ethylhexanol, tridecanol, stearyl alcohol, palmityl alcohol, cyclobutanol, cyclopentanol, cyclohexanol, benzyl alcohol, 2-phenylethanol, 2-(p-methoxyphenyl)-ethanol, 2-(3,4-dimethoxyphenyl)ethanol, 1-phenyl-3-butanol, ethanolamine, n-propanolamine, isopropanolamine, 2-amino-1-propanol, 1-methoxy-2-propanol, 3-amino-2,2-dimethyl-1-propanol, n-pentanolamine (1-amino-5-pentanol), n-hexanol-amine (1-amino-6-hexanol), ethanolamine, diethanolamine, triethanolamine, N-alkyl-diethanolamines, diisopropanolamine, 3-(2-hydroxyethylamino)propan-1-ol, 2-(N,N-dimethylamino)ethanol, 2-(N,N-diethylamino)ethanol, 2-(N,N-di-n-propylamino)ethanol, 2-(N,N-diisopropylamino)ethanol, 2-(N,N-di-n-butylamino)ethanol, 2-(N,N-diisobutyl-amino)ethanol, 2-(N,N-di-sec-butylamino)ethanol, 2-(N,N-di-tert-butylamino)ethanol, 3-(N,N-dimethylamino)propanol, 3-(N,N-diethylamino)propanol, 3-(N,N-di-n-propylamino)propanol, 3-(N,N-diisopropylamino)propanol, 3-(N,N-di-n-butylamino)propanol, 3-(N,N-diisobutylamino)propanol, 3-(N,N-di-sec-butylamino)-propanol, 3-(N,N-di-tert-butylamino)propanol, 1-dimethylaminopentanol-4,1-di-ethylaminopentanol-4, ethylene glycol, 1,2-propylene glycol, 1,3-propylene glycol, diglycol, 1,4-butanediol, 1,5-pentanediol, 1,6-hexanediol, 2,2-bis[4-hydroxycyclohexyl]propane, methoxyethanol, propoxyethanol, butoxyethanol, polypropyl alcohols, polyethylene glycol ethers, polypropylene glycol ethers and polybutylene glycol ethers. The latter polyalkylene glycol ethers are converted to the corresponding amines in the inventive reaction by converting their free hydroxyl groups.

Particularly preferred alcohols are methanol, ethanol, n-propanol, i-propanol, n-butanol, sec-butanol, 1,4-butanediol, 1,5-pentanediol, 1,6-hexanediol, 2-ethylhexanol, cyclohexanol, fatty alcohols, ethylene glycol, diethylene glycol (DEG), triethylene glycol (TEG), 2-(2-dimethylaminoethoxy)ethanol, N-methyldiethanolamine and 2-(2-di-methylaminoethoxy)ethanol.

Suitable ketones usable in the process according to the invention are, under the abovementioned prerequisites, virtually all aliphatic and aromatic ketones. The aliphatic ketones may be straight-chain, branched or cyclic; the ketones may comprise heteroatoms. The ketones may further bear substituents or comprise functional groups which behave inertly under the conditions of the hydrogenating amination, for example alkoxy, alkenyloxy, alkylamino or dialkylamino groups, or else, if appropriate, are hydrogenated under the conditions of the hydrogenating amination, for example C—C double or triple bonds. When polyfunctional ketones are to be aminated, it is possible via the control of the reaction conditions to obtain amino ketones, amino alcohols, cyclic amines or polyaminated products.

Preference is given, for example, to aminatingly hydrogenating the following ketones:

acetone, ethyl methyl ketone, methyl vinyl ketone, isobutyl methyl ketone, butanone, 3-methylbutan-2-one, diethyl ketone, tetralone, acetophenone, p-methylacetophenone, p-methoxyacetophenone, m-methoxyacetophenone, 1-acetylnaphthalene, 2-acetyl-naphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone.

Suitable aldehydes usable in the process according to the invention are, under the abovementioned prerequisites, virtually all aliphatic and aromatic aldehydes. The aliphatic aldehydes may be straight-chain, branched or cyclic; the aldehydes may comprise heteroatoms. The aldehydes may further bear substituents or comprise functional groups which behave inertly under the conditions of the hydrogenating amination, for example alkoxy, alkenyloxy, alkylamino or dialkylamino groups, or else, if appropriate, are hydrogenated under the conditions of the hydrogenating amination, for example C—C double or triple bonds. When polyfunctional aldehydes or keto aldehydes are to be aminated, it is possible via the control of the reaction conditions to obtain amino alcohols, cyclic amines or polyaminated products.

Preference is given, for example, to aminatingly hydrogenating the following aldehydes:

formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methyl-pentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, lysmeral, acrolein, methacrolein, ethylacrolein, citral, crotonaldehyde, 3-methoxypropionaldehyde, 3-aminopropionaldehyde, hydroxypivalaldehyde, dimethylolpropionaldehyde, dimethylolbutyraldehyde, furfural, glyoxal, glutaraldehyde and hydroformylated oligomers and polymers, for example hydroformylated polyisobutene (polyisobutenealdehyde) or hydroformylated oligomer obtained by metathesis of 1-pentene and cyclopentene.

The aminating agents used in the hydrogenating amination of alcohols, aldehydes or ketones in the presence of hydrogen may be either ammonia or primary or secondary, aliphatic or cycloaliphatic or aromatic amines.

When the aminating agent used is ammonia, the alcoholic hydroxyl group or the aldehyde group or the keto group is initially converted to the primary amino groups (—NH$_2$). The primary amine thus formed may react with further alcohol or aldehyde or ketone to give the corresponding secondary amine and this may in turn react with further alcohol or aldehyde or ketone to give the corresponding, preferably symmetrical, tertiary amine. Depending on the composition of the reaction mixture or of the reactant stream (in continuous mode), and depending on the reaction conditions employed—pressure, temperature, reaction time (catalyst hourly space velocity)—it is possible in this way to prepare preferentially primary, secondary or tertiary amines as desired.

In this way, it is possible to prepare, from polyhydric alcohols or di- or oligoaldehydes or di- or oligoketones or keto aldehydes, by intramolecular hydrogenating amination, cyclic amines, for example pyrrolidines, piperidines, hexamethyleneimines, piperazines and morpholines.

As well as ammonia, the aminating agents used may equally be primary or secondary amines.

These aminating agents are preferably used to prepare unsymmetrically substituted di- or trialkylamines, such as ethyldiisopropylamine and ethyldicyclohexylamine. For example the following mono- and dialkylamines are used as aminating agents: monomethylamine, dimethylamine, monoethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, iso-hexylamine, cyclohexylamine, aniline, toluidine, piperidine, morpholine and pyrrolidine.

Amines prepared with particular preference by the process according to the invention are, for example, morpholine (from monoaminodiglycol), monoaminodiglycol, morpholine and/or 2,2'-dimorpholinodiethyl ether (DMDEE) (from DEG and ammonia), 6-dimethylaminohexanol-1 (from hexanediol and dimethylamine (DMA)), triethylamine (from ethanol and diethylamine (DEA)), dimethylethylamine (from ethanol and DMA), N—($C_{1-4}$-alkyl)morpholine (from DEG and mono($C_{1-4}$-alkyl)amine), N—($C_{1-4}$-alkyl)piperidine (from 1,5-pentanediol and mono($C_{1-4}$-alkyl)amine), piperazine and/or diethylenetriamine (DETA) (from N-(2-aminoethyl)ethanolamine (AEEA) and ammonia), N-methylpiperazine (from diethanolamine and MMA), N,N'-dimethylpiperazine (from N-methyldiethanolamine and MMA), 1,2-ethylenediamine (EDA) and/or diethylenetriamine (DETA) and/or PIP (from monoethanolamine (MEOA) and ammonia), 2-ethylhexylamine and bis(2-ethylhexyl)amine (from 2-ethylhexanol and $NH_3$), tridecylamine and bis(tridecyl)amine (from tridecanol and $NH_3$), n-octylamine (from n-octanol and $NH_3$), 1,2-propylenediamine (from 2-hydroxypropylamine and $NH_3$), 1-diethylamino-4-aminopentane (from 1-diethylamino-4-hydroxypentane and $NH_3$), N,N-di($C_{1-4}$-alkyl)cyclohexylamine (from cyclohexanone and/or cyclohexanol and di($C_{1-4}$-alkyl)amine), e.g. N,N-dimethyl-N-cyclohexylamine (DMCHA), polyisobuteneamine (PIBA; where, for example, n~1000) (from polyisobutenealdehyde and $NH_3$), N,N-diisopropyl-N-ethylamine (Hünig's base) (from N,N-diisopropylamine and acetaldehyde), N-methyl-N-isopropylamine (MMIPA) (from monomethylamine and acetone), n-propylamines (such as mono-/di-n-propylamine, N,N-dimethyl-N-n-propylamine (DMPA)) (from propionaldehyde and/or n-propanol and $NH_3$ or DMA), N,N-dimethyl-N-isopropylamine (DMIPA) (from i-propanol and/or acetone and DMA), N,N-dimethyl-N-butylamines (1-, 2- or isobutanol and/or butanal, i-butanal or butanone and DMA), 2-(2-di($C_{1-4}$-alkyl)aminoethoxy)ethanol and/or bis(2-di($C_{1-4}$-alkyl)aminoethyl)ether (from DEG and di($C_{1-4}$-alkyl)amine), 1,2-ethylenediamine (EDA), monoethanolamine (MEOA), diethylenetriamine (DETA) and/or piperazine (PIP) (from monoethylene glycol (MEG) and ammonia), 1,8-diamino-3,6-dioxaoctane and/or 1-amino-8-hydroxy-3,6-dioxaoctane (from triethylene glycol (TEG) and ammonia), 1-methoxy-2-propylamine (1-methoxyisopropylamine, MOIPA) (from 1-methoxy-2-propanol and ammonia), N-cyclododecyl-2,6-dimethylmorpholine (dodemorph) (from cyclododecanone and/or cyclododecanol and 2,6-dimethylmorpholine), polyetheramine (from corresponding polyether alcohol and ammonia). The polyether alcohols are, for example, polyethylene glycols or polypropylene glycols having a molecular weight in the range from 200 to 5000 g/mol; the corresponding polyetheramines are obtainable, for example, under the tradename PEA D230, D400, D2000, T403 or T5000 from BASF.

All pressure figures are based on the absolute pressure.

EXAMPLES

Comparative Example 1

Preparation of an amination catalyst based on Ni—Co—Cu/$ZrO_2$ (Comparative Experiment According to EP 963 975 A)

An aqueous solution of nickel nitrate, cobalt nitrate, copper nitrate and zirconium acetate which comprised 2.39% by weight of NiO, 2.39% by weight of CoO, 0.94% by weight of CuO and 2.82% by weight of $ZrO_2$ was precipitated simultaneously in a stirred vessel in a constant stream with a 20% by weight aqueous sodium carbonate solution at a temperature of 70° C. in such a way that the pH, measured with a glass electrode, of 7.0 was maintained. The resulting suspension was filtered and the filtercake was washed with demineralized water until the electrical conductivity of the filtrate was approx. 20 µS. Thereafter, the filtercake was dried at a temperature of 150° C. in a drying cabinet or a spray dryer. The hydroxide-carbonate mixture obtained in this way was then calcined at a temperature of 450 to 500° C. over a period of 4 hours. The catalyst thus prepared had the composition: 28% by weight of NiO, 28% by weight of CoO, 11% by weight of CuO and 33% by weight of $ZrO_2$.

The catalyst was mixed with 3% by weight of graphite and shaped to tablets. The oxidic tablets were reduced. The reduction was performed at 280° C. at a heating rate of 3° C./minute. Reduction was effected first with 10% $H_2$ in $N_2$ for 50 minutes, then with 25% $H_2$ in $N_2$ for 20 minutes, then with 50% $H_2$ in $N_2$ for 10 minutes, then with 75% $H_2$ in $N_2$ for 10 minutes and finally with 100% $H_2$ for 3 hours. The percentages are each % by volume. The passivation of the reduced catalyst was performed at room temperature in dilute air (air in $N_2$ with a maximum $O_2$ content of 5% by volume).

Comparative Example 2

Preparation of an Amination Catalyst Based on Ni—Cu—Mo/$ZrO_2$ (Comparative Experiment According to EP 696 572 A)

An aqueous solution of nickel nitrate, copper nitrate and zirconium acetate which comprised 4.48% by weight of Ni (calculated as NiO), 1.52% by weight of Cu (calculated as CuO) and 2.28% by weight of Zr (calculated as $ZrO_2$) was coprecipitated in a stirred vessel in a constant stream with a 20% by weight aqueous sodium carbonate solution at a temperature of 70° C. in such a way that the pH, measured with a glass electrode, of 7.0 was maintained. The resulting suspension was filtered and the filtercake was washed with demineralized water until the electrical conductivity of the filtrate was approx. 20 µS. Thereafter, 12.9 g of ammonium heptamolybdate per 50 g of nickel salt, calculated as NiO, were incorporated into the still-moist filtercake, so as to obtain the oxide mixture specified below. Subsequently, the filtercake was dried at a temperature of 150° C. in a drying cabinet or a spray dryer. The dried hydroxide-carbonate mixture was subsequently calcined at a temperature of 430 to 460° C. over a period of 4 hours. The catalyst thus prepared had the following composition: 50% by weight of NiO, 17% by weight of CuO, 1.5% by weight of $MoO_3$ and 31.5% by weight of $ZrO_2$.

The catalyst thus obtained was admixed with 3% by weight of graphite, compacted and finally shaped to tablets. The tablets were subsequently reduced. The reduction was performed at 290° C. with a mixture consisting of 20% by volume of hydrogen and 80% by volume of nitrogen at a heating rate of 3° C./minute. The passivation of the reduced catalyst was performed at room temperature in dilute air (air in $N_2$ with an $O_2$ content of not more than 5% by volume).

Comparative Example 3

Preparation of an Amination Catalyst Based on Ni—Co—Cu—Sn/ZrO$_2$ (Comparative Experiment According to WO 2008/006750 A1)

The catalyst was prepared analogously to comparative example 1, except that the amounts of nickel nitrate, of copper nitrate and of cobalt nitrate were altered correspondingly, and tin dichloride was additionally added to the nitrate solution. The hydroxide-carbonate mixture obtained in the above manner was calcined at a temperature of 450° C. over a period of 4 hours. The material thus obtained was admixed with 3% by weight of graphite, compacted and finally shaped to tablets. The tablets were subsequently reduced. The reduction was performed at 290° C. with a mixture consisting of 20% by volume of hydrogen and 80% by volume of nitrogen at a heating rate of 3° C./minute. The passivation of the reduced catalyst was performed at room temperature in dilute air (air in $N_2$ with an $O_2$ content of not more than 5% by volume). The catalyst thus obtained had the composition as stated in the table I below.

Example 4

Inventive

An aqueous solution of nickel nitrate, cobalt nitrate, copper nitrate, aluminum nitrate and tin(II) chloride, which comprised 3.9% Ni, 3.9% Co, 1.9% Cu, 5.5% $Al_2O_3$ and 0.5% Sn, was coprecipitated in a stirred vessel in a constant stream with a 20% by weight aqueous sodium carbonate solution at a temperature of 65-70° C., in such a way that the pH, measured with a glass electrode, of 5.7 was maintained. After the precipitation, air was blown in for 1 hour, then the pH of the solution was adjusted to the value of 7.4 with sodium carbonate solution. The resulting suspension was filtered and the filtercake was washed with demineralized water until the electrical conductivity of the filtrate was approx. 20 mS. Thereafter, the filtercake was dried in a drying cabinet at a temperature of 150° C. The hydroxide-carbonate mixture obtained in this way was then calcined at a temperature of 500° C. over 4 hours. The catalyst material was subsequently mixed with 3% by weight of graphite and shaped to 3×3 mm tablets. The tablets obtained in this way are reduced in hydrogen at a temperature of 280-300° C. over at least 12 hours. The passivation of the reduced catalyst was performed at room temperature in dilute air (air in $N_2$ with an $O_2$ content of not more than 5% by volume). The catalyst thus obtained had the composition as shown in table I below.

Example 5

Inventive

The catalyst was prepared analogously to comparative example 3, except that the amounts of nickel nitrate, of copper nitrate, of cobalt nitrate and of tin chloride were altered correspondingly. Instead of zirconium acetate solution, finely dispersed aluminum oxide powder (D10-10 from BASF SE) was stirred in.

The hydroxide-carbonate mixture obtained in the above-specified manner was calcined at a temperature of 450° C. over a period of 4 hours. The material thus obtained was admixed with 3% by weight of graphite, compacted and finally shaped to tablets. The tablets were subsequently reduced. The reduction was performed at 290° C. with a mixture consisting of 20% by volume of hydrogen and 80% by volume of nitrogen, at a heating rate of 3° C./minute. The passivation of the reduced catalyst was performed at room temperature in dilute air (air in $N_2$ with an $O_2$ content of not more than 5% by volume). The catalyst thus obtained had the composition as shown in table I below.

Performance of the Catalysis Tests in a Continuous Tubular Reactor

Amination of Diethylene Glycol (DEG)

A heated tubular reactor with internal diameter 14 mm, a centrally mounted thermocouple and a total volume of 89 ml was charged in the lower section with a layer of glass beads (15 ml), on top of that with 30 ml of the reduced amination catalyst (in the form of approx. 1.0-1.6 mm spall, which was produced from the reduced and passivated tablets), and finally the remaining part again with glass beads. Prior to the reaction, the catalyst was activated at max. 280° C. under hydrogen (25 l (STP)/h) (l (STP)=standard liters=volume converted to standard conditions (20° C., 1 bar abs.)) at standard pressure for 24 hours. 35 g/h of DEG, 35 g/h of liquid $NH_3$ and 7 l (STP)/h of hydrogen were metered through the reactor from the bottom upward. The reactor was kept at a temperature of approx. 190 to 210° C. and total pressure 200 bar. The reaction temperature was selected so as to attain a DEG conversion of approx. 65-70%. The mixture leaving the reactor was cooled and decompressed to standard pressure. At different times, samples were taken from the reaction mixture and analyzed by means of gas chromatography. For this purpose, an "RTX-5 amine" GC column of length 30 m was used, with a temperature program: 80° C./15 minutes, heat to 290° C. within 30 minutes, at 290° C./15 minutes.

The composition of the resulting reaction mixtures for the catalysts of examples 1 to 5 can be found in table II below.

TABLE I

| Catalyst*) | Ni % | Co % | Cu % | Sn % | Mo % | BET**) m$^2$/g | Support |
|---|---|---|---|---|---|---|---|
| Comparative ex. 1 | 21.9 | 21.9 | 10.5 | — | — | 90 | ZrO2 |
| Comparative ex. 2 | 45.0 | — | 12.0 | — | 1.5 | 85 | ZrO2 |
| Comparative ex. 3 | 18.7 | 18.0 | 10.2 | 1.0 | — | 62 | ZrO2 |
| Example 4 | 18.6 | 17.3 | 10.6 | 1.1 | — | 187 | Al2O3 |
| Example 5 | 17.6 | 17.3 | 9.7 | 0.9 | — | 154 | Al2O3 |

*)Catalyst composition in % by weight; remainder up to 100% by weight is the support
**)ISO 9277:1995

TABLE II

| Catalyst | Amount of cat. ml | g | TOS h | Temp. °C. | Space velocity kg/lcat·h | MR | DEG conversion mol % | ADG mol % | MOR mol % | Ratio ADG/MOR | Overall select. mol % | Methoxy GC % | EC GC % |
|---|---|---|---|---|---|---|---|---|---|---|---|---|---|
| Comparative Ex. 1 | 30 | 37.7 | 142 | 190 | 1.2 | 6.2 | 72.5 | 40.2 | 47.3 | 0.85 | 89.2 | 0.230 | 0.62 |
| | | | 246 | 190 | 1.2 | 6.2 | 70.7 | 39.9 | 48.2 | 0.83 | 89.8 | 0.220 | 0.57 |
| Comparative Ex. 2 | 30 | 36.8 | 136 | 193 | 1.2 | 6.2 | 69.4 | 55.6 | 32.8 | 1.69 | 90.2 | 0.170 | 1.17 |
| | | | 236 | 193 | 1.2 | 6.2 | 69.2 | 55.3 | 33.5 | 1.65 | 90.7 | 0.151 | 1.00 |
| Comparative Ex. 3 | 27 | 27.5 | 186 | 193 | 1.0 | 6.2 | 71.8 | 46.1 | 42.5 | 1.08 | 91.4 | 0.061 | 0.31 |
| | | | 282 | 193 | 1.0 | 6.2 | 70.4 | 47.2 | 41.6 | 1.13 | 91.6 | 0.059 | 0.27 |
| Example 4 | 30 | 20.7 | 75 | 198 | 1.2 | 6.2 | 75.1 | 52.4 | 37.5 | 1.40 | 93.0 | 0.050 | 0.14 |
| | | | 236 | 198 | 1.2 | 6.2 | 66.7 | 60.4 | 29.7 | 2.03 | 93.1 | 0.030 | 0.15 |
| | | | 356 | 198 | 1.2 | 6.2 | 58.1 | 65.6 | 25.2 | 2.60 | 93.4 | 0.030 | 0.13 |
| Example 5 | 30 | 24.8 | 141 | 208 | 1.2 | 6.2 | 70.9 | 61.0 | 31.1 | 1.96 | 96.6 | 0.079 | 0.32 |
| | | | 196 | 208 | 1.2 | 6.2 | 67.6 | 65.1 | 26.9 | 2.42 | 96.5 | 0.065 | 0.31 |

TOS: time on stream (hours)
Temp.: Temperature in the reactor
MR: Molar ammonia/DEG ratio in the feed
Overall select.: Overall selectivity; sum of ADG + MOR + di-ADG (mol %)
Methoxy: Methoxyethanol in the crude discharge (GC %)
EC: Ether cleavage component; sum of ethanol, ethylamine, ethylmorpholine in the crude discharge (GC %)

Workup:

The particular pure products can be obtained by the known methods from the aqueous raw materials, by rectification under reduced pressure, standard pressure or elevated pressure. The pure products are obtained either directly in pure form or as azeotropes with water. Aqueous azeotropes can be dewatered by a liquid-liquid extraction with concentrated sodium hydroxide solution before or after the purifying distillation. Distillative dewatering in the presence of an entraining agent by known methods is also possible.

In the case that the raw material or the aliphatic amine in the raw material is barely water-miscible or water-immiscible, dewatering by a separation of the organic and aqueous phases by known methods is also possible.

Conclusion:

The performance of amination catalysts has been improved significantly compared to the prior art while maintaining the good catalyst activity, by altering the chemical composition of the active material in accordance with the invention. The yield of amination products of economic interest, such as aminodiglycol and morpholine in the DEG amination, can be increased by using a corresponding catalyst with $Al_2O_3$ as the support in combination with Ni, Co, Cu and Sn. More particularly, the yield of valuable linear amination products, such as aminodiglycol in the DEG amination, can be enhanced. In addition, the extent of undesired decarbonylation, which is determined by the content of methoxyethanol in the DEG amination, and of ether cleavage can be reduced significantly.

The invention claimed is:

1. A process for preparing an amine by reacting a primary or secondary alcohol, aldehyde and/or ketone with hydrogen and a nitrogen compound selected from the group of ammonia and primary and secondary amines, in the presence of a supported copper-, nickel- and cobalt-containing catalyst, wherein the catalytically active material of the catalyst, before the reduction thereof with hydrogen, comprises oxygen compounds of aluminum, of copper, of nickel and of cobalt, and in the range from 0.2 to 5.0% by weight of oxygen compounds of tin, calculated as SnO.

2. The process according to claim 1, wherein the catalytically active material of the catalyst, before the reduction thereof with hydrogen, comprises in the range from 0.4 to 4.0% by weight of oxygen compounds of tin, calculated as SnO.

3. The process according to claim 1, wherein the catalytically active material of the catalyst, before the reduction thereof with hydrogen, comprises in the range from 0.6 to 3.0% by weight of oxygen compounds of tin, calculated as SnO.

4. The process according to claim 1, wherein the catalytically active material of the catalyst, before the reduction thereof with hydrogen, comprises in the range from 5.0 to 35% by weight of oxygen compounds of cobalt, calculated as CoO.

5. The process according to claim 1, wherein the catalytically active material of the catalyst, before the reduction thereof with hydrogen, comprises in the range from 10 to 30% by weight of oxygen compounds of cobalt, calculated as CoO.

6. The process according to claim 1, wherein the catalytically active material of the catalyst, before the reduction thereof with hydrogen, comprises in the range from 15 to 80% by weight of oxygen compounds of aluminum, calculated as $Al_2O_3$, 1.0 to 20% by weight of oxygen compounds of copper, calculated as CuO, and 5.0 to 35% by weight of oxygen compounds of nickel, calculated as NiO.

7. The process according to claim 1, wherein the catalytically active material of the catalyst, before the reduction thereof with hydrogen, comprises in the range from 30 to 70% by weight of oxygen compounds of aluminum, calculated as $Al_2O_3$, 2.0 to 18% by weight of oxygen compounds of copper, calculated as CuO, and 10 to 30% by weight of oxygen compounds of nickel, calculated as NiO.

8. The process according to claim 1, wherein the molar ratio of nickel to copper in the catalyst is greater than 1.

9. The process according to claim 1, wherein the catalytically active material of the catalyst does not comprise any rhenium and/or ruthenium.

10. The process according to claim 1, wherein the catalytically active material of the catalyst does not comprise any iron and/or zinc.

11. The process according to claim 1, wherein the catalytically active material of the catalyst does not comprise any oxygen compounds of silicon and/or of zirconium.

12. The process according to claim 1, wherein the BET surface area of the catalyst (ISO 9277:1995) is in the range from 30 to 250 $m^2/g$.

13. The process according to claim 1, wherein the reaction is performed at a temperature in the range from 80 to 350° C.

14. The process according to claim 1, wherein the reaction is performed in the liquid phase at an absolute pressure in the range from 5 to 30 MPa, or in the gas phase at an absolute pressure in the range from 0.1 to 40 MPa.

15. The process according to claim 1, wherein the amine component (nitrogen compound) is used in 0.90 to 100 times the molar amount based on the alcohol, aldehyde and/or ketone used.

16. The process according to claim 1, wherein the catalyst is arranged as a fixed bed in the reactor.

17. The process according to claim 1, which is performed continuously.

18. The process according to claim 17, wherein the reaction is effected in a tubular reactor.

19. The process according to claim 17, wherein the reaction is effected in a cycle gas method.

20. The process according to claim 1, wherein the alcohol, aldehyde and/or ketone is used as an aqueous solution.

21. The process according to claim 1, wherein the ammonia or the primary or secondary amine is used as an aqueous solution.

22. The process according to claim 1 for preparing monoaminodiglycol (ADG) and morpholine by reacting diethylene glycol (DEG) with ammonia.

23. The process according claim 1 for preparing N-($C_{1-4}$-alkyl)-morpholine by reacting diethylene glycol (DEG) with mono($C_{1-4}$-alkyl)amine.

24. The process according to claim 1 for preparing 2-(2-di($C_{1-4}$-alkyl)aminoethoxy)ethanol and/or bis(2-di($C_{1-4}$-alkyl)aminoethyl) ether by reacting diethylene glycol (DEG) with di($C_{1-4}$-alkyl)amine.

25. The process according claim 1 for preparing monoethanolamine (MEOA) and/or 1,2-ethylenediamine (EDA) by reacting monoethylene glycol (MEG) with ammonia.

26. The process according to claim 1 for preparing 1,2-ethylenediamine 6(EDA) by reacting monoethanolamine (MEOA) with ammonia.

27. The process according to claim 1 for preparing a polyetheramine by reacting a corresponding polyether alcohol with ammonia.

28. The process according to claim 1 for preparing piperazine and/or diethylenetriamine (DETA) by reacting N-(2-aminoethyl)ethanolamine (AEEA) with ammonia.

29. The process according claim 1 for preparing polyisobuteneamine (PIBA) by reacting polyisobutenealdehyde with ammonia.

30. A catalyst, wherein the catalytically active material of the catalyst, before the reduction thereof with hydrogen, comprises oxygen compounds of aluminum, of copper, of nickel and of cobalt, and in the range from 0.2 to 5.0% by weight of oxygen compounds of tin, calculated as SnO.

31. The catalyst according to claim 30, wherein the catalytically active material of the catalyst, before the reduction thereof with hydrogen, comprises in the range from 0.4 to 4.0% by weight of oxygen compounds of tin, calculated as SnO.

32. The catalyst according to claim 30, wherein the catalytically active material of the catalyst, before the reduction thereof with hydrogen, comprises in the range from 0.6 to 3.0% by weight of oxygen compounds of tin, calculated as SnO.

33. The catalyst according to claim 30, wherein the catalytically active material of the catalyst, before the reduction thereof with hydrogen, comprises in the range from 5.0 to 35% by weight of oxygen compounds of cobalt, calculated as CoO.

34. The catalyst according to claim 30, wherein the catalytically active material of the catalyst, before the reduction thereof with hydrogen, comprises in the range from 10 to 30% by weight of oxygen compounds of cobalt, calculated as CoO.

35. The catalyst according to claim 30, wherein the catalytically active material of the catalyst, before the reduction thereof with hydrogen, comprises in the range from
    15 to 80% by weight of oxygen compounds of aluminum, calculated as $Al_2O_3$,
    1.0 to 20% by weight of oxygen compounds of copper, calculated as CuO, and
    5.0 to 35% by weight of oxygen compounds of nickel, calculated as NIO.

36. The catalyst according to claim 30, wherein the catalytically active material of the catalyst, before the reduction thereof with hydrogen, comprises in the range from
    30 to 70% by weight of oxygen compounds of aluminum, calculated as $Al_2O_3$,
    2.0 to 18% by weight of oxygen compounds of copper, calculated as CuO, and
    10 to 30% by weight of oxygen compounds of nickel, calculated as NiO.

37. The catalyst according to claim 30, wherein the molar ratio of nickel to copper in the catalyst is greater than 1.

38. The catalyst according to claim 30, wherein the catalytically active material of the catalyst does not comprise any rhenium and/or ruthenium.

39. The catalyst according to claim 30, wherein the catalytically active material of the catalyst does not comprise any iron and/or zinc.

40. The catalyst according to claim 30, wherein the catalytically active material of the catalyst does not comprise any oxygen compounds of silicon and/or of zirconium.

41. The catalyst according to claim 30, wherein the BET surface area of the catalyst (ISO 9277:1995) is in the range from 30 to 250 $m^2/g$.

* * * * *